United States Patent [19]
Fischer et al.

[11] Patent Number: 6,139,820
[45] Date of Patent: *Oct. 31, 2000

[54] DELIVERY SYSTEM FOR DENTAL AGENTS

[75] Inventors: Dan E. Fischer, Sandy; Steven D. Jensen, South Jordan, both of Utah

[73] Assignee: Ultradent Products, Inc., South Jordan, Utah

[ * ] Notice: This patent is subject to a terminal disclaimer.

[21] Appl. No.: 09/360,998

[22] Filed: Jul. 26, 1999

Related U.S. Application Data

[63] Continuation-in-part of application No. 09/181,103, Oct. 28, 1998, Pat. No. 6,010,683, which is a continuation-in-part of application No. 08/964,502, Nov. 5, 1997, abandoned.

[51] Int. Cl.[7] .................... A61K 7/16; A61K 7/18
[52] U.S. Cl. .................................. 424/52; 424/49
[58] Field of Search ......................... 424/49–88

[56] References Cited

U.S. PATENT DOCUMENTS

| | | | |
|---|---|---|---|
| 2,968,928 | 1/1961 | Reed | 252/305 |
| 2,995,521 | 8/1961 | Estignard-Bluard | 252/90 |
| 3,011,950 | 12/1961 | Mehaffey | 167/85 |
| 3,105,612 | 10/1963 | Krasnoff et al. | 222/78 |
| 3,422,993 | 1/1969 | Boehm et al. | 222/190 |
| 3,694,546 | 9/1972 | Roth et al. | 424/45 |
| 3,707,771 | 1/1973 | Guerra | 32/19 |
| 3,709,437 | 1/1973 | Wright | 239/343 |
| 3,791,098 | 2/1974 | Webster | 53/30 |
| 3,858,764 | 1/1975 | Watson | 222/399 |
| 3,937,235 | 2/1976 | Broughton | 132/84 B |
| 3,937,364 | 2/1976 | Wright | 222/190 |
| 3,946,108 | 3/1976 | Tomlinson et al. | 424/49 |
| 3,947,567 | 3/1976 | Berg, Jr. et al. | 424/45 |
| 3,955,942 | 5/1976 | Cordon et al. | 51/295 |
| 3,964,649 | 6/1976 | Alexander | 222/399 |
| 3,985,668 | 10/1976 | Hartman | 252/99 |
| 3,988,433 | 10/1976 | Benedict | 424/53 |
| 4,018,364 | 4/1977 | Wright | 222/190 |
| 4,022,351 | 5/1977 | Wright | 222/145 |
| 4,027,789 | 6/1977 | Dickey | 222/190 |
| 4,047,645 | 9/1977 | Caliendo | 222/386.5 |
| 4,051,056 | 9/1977 | Hartman | 252/99 |
| 4,066,745 | 1/1978 | Tomlinson et al. | 424/49 |
| 4,093,123 | 6/1978 | Maran | 239/322 |
| 4,102,992 | 7/1978 | Davis | 424/49 |
| 4,111,713 | 9/1978 | Beck | 106/288 |
| 4,143,126 | 3/1979 | Gaffar | 424/49 |
| 4,184,615 | 1/1980 | Wright | 222/190 |
| 4,588,582 | 5/1986 | Motarjemi | 424/49 |
| 4,651,905 | 3/1987 | Hayes | 222/394 |
| 4,770,634 | 9/1988 | Pellico | 433/217.1 |
| 4,834,969 | 5/1989 | Grollier | 424/49 |
| 4,836,422 | 6/1989 | Rosenberg | 222/190 |
| 4,969,577 | 11/1990 | Werding | 222/94 |
| 4,995,533 | 2/1991 | Vandoninck | 222/54 |

(List continued on next page.)

FOREIGN PATENT DOCUMENTS

| | | | |
|---|---|---|---|
| 1319875 | 7/1993 | Canada | 134/44 |
| WO 82/03975 | 11/1982 | WIPO . | |

*Primary Examiner*—Shep K. Rose
*Attorney, Agent, or Firm*—Workman, Nydegger, Seeley

[57] ABSTRACT

Toothpaste and other dentifrices formulated to include a volume increasing agent (density reducing agent) in order to significantly increase the volume of the toothpaste at the time it is dispensed onto a toothbrush. The inventive dental compositions preferably include a substantial quantity of entrained or trapped air or other gas in order to reduce the density, and hence the weight, of toothpaste actually placed within a person's mouth. The result is a reduction in the amount of active ingredients introduced into a person's mouth that might be ingested. The entrained air or other gas can also increase the availability of the active ingredient since the foamed composition increases the dispersibility of the active ingredients within saliva. The net effect is that a person decreases the actual amount of toothpaste without decreasing the volume, or visual amount, of toothpaste dispensed on the toothbrush. The density-reduction effect can alternatively be provided by means of a lower density filler in addition to, or instead of, the entrained gas. Such fillers typically include trapped air or voids.

36 Claims, 1 Drawing Sheet

U.S. PATENT DOCUMENTS

| | | | |
|---|---|---|---|
| 5,048,750 | 9/1991 | Tobler | 222/189 |
| 5,071,637 | 12/1991 | Pellico | 424/45 |
| 5,073,363 | 12/1991 | Pellico | 424/49 |
| 5,090,595 | 2/1992 | Vandoninck | 222/54 |
| 5,110,583 | 5/1992 | Sampathkumar | 242/48 |
| 5,124,143 | 6/1992 | Müllemann et al. | 424/49 |
| 5,230,648 | 7/1993 | Kelley et al. | 446/74 |
| 5,266,304 | 11/1993 | Baffelli et al. | 424/49 |
| 5,407,287 | 4/1995 | Braun et al. | 401/176 |
| 5,597,553 | 1/1997 | Baffelli et al. | 424/49 |
| 5,665,332 | 9/1997 | Mundschenk et al. | 424/49 |
| 5,736,158 | 4/1998 | Quast | 424/464 |
| 5,824,289 | 10/1998 | Stoltz | 424/45 |

DELIVERY SYSTEM FOR DENTAL AGENTS

RELATED APPLICATIONS

This application is a continuation-in-part of U.S. application Ser. No. 09/181,103, filed Oct. 28, 1998 now issued U.S. Pat. No. 6,010,683, which is a continuation-in-part of U.S. application Ser. No. 08/964,502, filed Nov. 5, 1997 (abandoned). For purposes of disclosure, the foregoing applications are incorporated herein by specific reference.

BACKGROUND OF THE INVENTION

1. The Field of the Invention

The present invention is in the field of oral dentifrices, particularly in the field of toothpastes. More particularly, the present invention relates to expanded toothpastes that have an increased volume-to-mass ratio in order to reduce the overall mass of toothpaste that is dispensed during each use. Such dentifrices deliver a lower absolute quantity of active ingredients while maintaining their legally required concentrations.

2. The Relevant Technology

Toothpastes and other dentifrices are widely used in America and throughout the world to provide good oral hygiene, to prevent tooth decay, remove stains and to treat or minimize other problems associated with oral hygiene, such as gum disease and foul breath odor. Toothpastes typically include an inert carrier gel or paste, abrasive agents for removing plaque and other impurities found on a person's teeth, decay preventing medicaments, such as fluorides flavorants, surfactants, detergents, and other additives to provide a desired consistency and cleansing or medicinal activity. While many ingredients may be added or eliminated according to fads or perceived specialized needs, such as baking soda or tartar removing agents, modern toothpastes almost uniformly include fluoride in one form or another.

Fluoride has been medically proven to aid in the prevention of tooth decay. Typically, tooth decay causing agents generally comprise acids formed by bacterial breakdown of sugars in a person's mouth. Enamel treated with fluoride is much more resistant to such acidic attack compared to enamel that has not been treated with fluoride.

Nevertheless, there are some problems associated with the careless use of fluoride. While topical administration of fluoride to teeth provides reduced tooth decay, fluorides can be harmful if ingested in large enough amounts. Ingesting too much fluoride can lead to fluorosis and even death in some cases. Even if sublethal doses of fluoride are ingested, a person with fluorosis will often develop brown, mottled enamel and/or bone dyscrasia and other abnormalities. Even lower levels of fluoride ingestion can cause significant tooth discoloration. In higher amounts, the fluoride can affect the structural formation of teeth and cause inappropriate development, particularly in children.

While fluorosis can affect persons of any age, it is particularly pronounced in children. This is because children are much smaller and have far less body mass compared to adults. In addition, their bodies are in the development stage so that health problems have a more permanent and long-term effect. Therefore, a quantity of fluoride that is safe when ingested by an adult might be harmful if ingested by a child.

Moreover, because children are generally resistant to certain hygienic practices, including brushing their teeth on a regular basis, toothpaste manufacturers have deliberately developed toothpaste that taste good to encourage brushing. While this might have the beneficial effect of encouraging more brushing by children, it has the negative side effect of enticing children to swallow the toothpaste while they brush. Depending on the taste, children may intentionally or unintentionally swallow substantial amounts of toothpaste. Moreover, children generally do not understand that it is not proper to swallow toothpaste and might swallow large amounts even though many toothpastes for children include a warning label against ingestion of the product. Much of the problem stems from the tendency of children to apply too much toothpaste onto the brush.

Because of the known dangers associated with ingesting high levels of fluoride, toothpaste manufacturers generally recommend that children use only a pea-size quantity of toothpaste on the brush. A "pea-size" amount is typically about ⅓ the amount of toothpaste needed to fully cover an adult-sized toothbrush, as seen on advertisements generally. While such warnings are certainly proper, they are often not understood and ignored by both adults and children alike. In general, children simply do not understand that fluoride, while beneficial in very low doses, can be a poison at higher levels.

In real-life situations, most humans including children will lay a solid strip of toothpaste across the entire length of the toothbrush bristles. This is not surprising since we are all familiar with the ubiquitous television and print advertisements showing an inviting and generous quantity of toothpaste that runs the length of the toothbrush bristles, and even curls artistically and invitingly up and around on the end to form a solid strip across the length of the toothbrush with a "curly-Q" on one end. It is obviously in the toothpaste manufacturer's best interest to encourage the use of larger quantities of toothpaste, even though wasteful, in order to cause faster toothpaste depletion and more subsequent sales.

Because of this reality, the unfortunate result is that children have been found to develop fluorosis, which causes brown, mottled enamel. In addition, even more moderate doses of fluoride can create discoloration affect structural formation of teeth, and cause diseased teeth and bones. It is possible that the dangers of fluoride ingestion by children might actually outweigh the benefits of fluoride in fighting tooth decay, at least in some cases.

In addition to fluoride, toothpastes can include other ingredients which, while beneficial when applied topically in the mouth, might have unwanted side effects if ingested. Other ingredients in toothpaste that should not be ingested include surfactants, agents used to fight gum disease, tartar removal agents, bleachants, and other cleansing or disinfecting agents that are intended for topical application only.

In light of the foregoing, what are needed are compositions and methods for manufacturing toothpastes and other dentifrices which reduced the level of fluoride and other active ingredients that might be ingested by adults or children while still providing their beneficial effects.

It would be an additional improvement in the art to provide compositions and methods for manufacturing toothpastes and other dentifrices that provided the desired concentration of active fluoride and other dental agents while reducing the amount delivered.

Moreover, it would be a marked improvement in the art to provide compositions and methods for manufacturing toothpastes and other dentifrices that yielded compositions having an increased rate of dispersion of the fluoride and/or other active ingredients into saliva or water within a person's mouth compared to conventional toothpastes.

In particular, it would be a tremendous improvement in the art to provide compositions and methods for manufacturing toothpastes and other dentifrices that had increased dispersibility in saliva such that the active dental agent, such as fluoride, is more rapidly available to effect its beneficial activity.

Such compositions and methods for manufacturing improved toothpastes and other dentifrices are disclosed and claimed herein.

SUMMARY AND OBJECTS OF THE INVENTION

The present invention relates to compositions and methods which reduce the quantity, but not the concentration, of active ingredients delivered in a dentifrice in order to limit the danger associated with their possible ingestion. Particularly, the present invention relates to expanded toothpastes and other dentifrices having an increased volume-to-mass ratio in order to provide what looks and feels like a desired quantity of toothpaste, while reducing the actual mass that is delivered. This can be accomplished by incorporating substantial amounts of air or other gases, either as a foam or in the form of porous lightweight fillers, which shall hereinafter be referred to as a "density reducing component" or "density reducing means". In both cases, the density reducing means or component involves a substantial quantity of void space, or gas, incorporated within the toothpaste.

Besides reducing the density of the toothpaste, trapped or entrained gas has the additional benefit of increasing the dispersibility of active ingredients within the dentifrice in order for there to be greater contact time between the active ingredients and the person's teeth. Foamed toothpastes or other dentifrices have greatly increased solubility in saliva, which provides for greater availability and increased uptake of the active ingredients by the teeth or surrounding tissues. They also reduce the actual amount of active ingredients placed within the person's mouth, thus reducing the risk of ingesting lethal or unhealthy quantities of active dental medicaments, such as fluoride, by children and incapacitated adults.

Whereas toothpaste manufacturers provide warning labels that state that children should use only a pea-sized quantity of toothpaste on the brush, this message is in small print and is also drowned out by the more seductive and persuasive advertising campaigns showing a generous quantity of toothpaste laid out as a solid, voluptuous strip across the brush. Because it is natural for people to want more of a "good thing", people naturally waste toothpaste in spite of warning labels. Even if a manufacturer teaches the benefits of using less toothpaste and chooses not to advertise the use of greater quantities, the images provided by other manufacturers may nevertheless stick in the public's mind and overwhelm a particular manufacturer's good intentions.

In light of the foregoing, the advantage of incorporating gas within the toothpaste is that it creates the illusion of having a large quantity of toothpaste. This illusion allows persons, particularly young children, to safely use a longer strip of toothpaste across the toothbrush bristles. The inventive toothpaste will, however, contain a significant volume of entrained or trapped gas such that the overall mass of toothpaste and active ingredients dispersed therein will typically be much lower than the visual appearance. This allows a child, for example, to cover the toothbrush with a longer strip of toothpaste, while delivering a much smaller quantity of actual toothpaste, since the strip is a mixture of toothpaste and an inert gas, lightweight filler or both.

Not only does a foamed toothpaste create the illusory effect of having more instead of less, the foam can have the additional advantage of causing the toothpaste or other dentifrice to mix and disperse more rapidly with saliva. This causes the toothpaste to more quickly spread across the teeth and into crevices to provide faster cleaning and treatment of the teeth. Thus, foaming the toothpaste causes it to have the ability to gain proximity to tooth surfaces and crevices far more quickly than conventional toothpastes. Because most people on average brush for 60 seconds or less, it is important that the fluoride or other active ingredients are rapidly deployed over the surface of the person's teeth. Otherwise, their intended benefit may not be realized to the extent desired.

Alternatively, the desired benefits can be provided by using a toothpaste dispenser or formulation that has the ability to foam the toothpaste in situ, or just prior to use, by the person dispensing the toothpaste. For example, a container of toothpaste can be provided in conjunction with a small compartment of compressed gas that could be mixed into and entrained within the toothpaste during the dispensing process in order to foam the toothpaste at the time of use. Alternatively, the toothpaste can include entrained gas and be stored under pressure in an initially unfoamed state. Upon dispensing, the compressed gas will expand and cause in situ foaming of the toothpaste, similar to how shaving foam behaves. The final result would essentially be the same as using pre-foamed toothpaste, but with lower initial volume.

It should be understood that virtually any toothpaste known in the art can be modified so that it includes substantial quantities of entrained air or other gas in order to create the aforementioned benefits of foamed toothpaste. Therefore, while the present application discusses certain preferred methods and/or additives that facilitate the formation of stable foamed toothpaste, it should be understood that any conventional toothpaste known in the art that incorporates substantial quantities of entrained gas or air such that a toothpaste of greatly reduced mass can be dispensed onto the user's toothbrush will be within the scope of the present invention. An example of a toothpaste composition known in the art is set forth in U.S. Pat. No. 3,988,433 to Benedict. There are presently a wide variety of unfoamed toothpastes in the market sold by companies such as Colgate-Palmolive and Proctor & Gamble. For purposes of disclosing conventional unfoamed toothpaste compositions, the foregoing patent and known commercial toothpaste compositions are incorporated herein by specific reference.

In order to manufacture a stable foamed toothpaste containing entrained air or other gas, the toothpaste composition will preferably include an appropriate foaming agent, one or more gelling or thickening agents, and an additional stabilizing agent for maintaining a stable foam. Depending on the desired level of aeration and the desired toothpaste consistency, the concentrations of thickening agent and stabilizer would generally need to be adjusted for a desired toothpaste formulation. For example, toothpastes that include greater quantities of air or other gas will generally need to include greater concentrations of thickening or gelling agents in order to maintain a desired stiffness or consistency, since the inclusion of greater quantities of entrained gas will tend to soften or liquify toothpaste compositions that would otherwise be more stiff or gel-like if lesser quantities of air were entrained. Moreover, toothpastes that include more entrained gas will generally require greater quantities of the foam stabilizing agent.

In many cases, toothpastes also include surfactants such as sodium laurel sulfate that cause them to foam when mixing with saliva. This helps to more quickly dissolve the toothpaste in the saliva and increase the uptake of medicaments such as fluoride. In the present invention, providing a toothpaste that is already foamed will create a more easily dissolvable toothpaste, thus reducing the need for added detergents. This has the benefit of reducing the potential for ingestion of detergents. While not usually toxic in most individuals, detergents can nevertheless cause some gastrointestinal discomfort.

In order to provide the foregoing benefits of increased dispersibility and availability of dispersed medicaments within toothpastes and other dentifrices, air or other gas may be entrained within the toothpaste or other dentifrice in an amount in a range from about 10% to about 90% by volume of the toothpaste or other dentifrice, preferably greater than about 25% by volume, more preferably greater than about 30% by volume, and most preferably greater than about 50% by volume of the toothpaste or other dentifrice. At lower concentrations of gas (i.e., below about 25% by volume), it will generally be necessary to include a second density reducing agent, such as a lightweight filler.

Instead of, or in addition to, incorporating substantial quantities of a gas, the inventive dentifrices may include the aforementioned lightweight solid filler. The term "lightweight solid" will refer to solid fillers that are generally insoluble in, and substantially impermeable to, the liquid components of the dentifrice and which preferably have a density less than about 0.50 g/cm$^3$, more preferably less than about 0.3 g/m$^3$, and most preferably less than about 0.1 g/cm$^3$. Because the lightweight solids can act to displace a substantial portion of the active dentifrice without substantially reducing its concentration, lightweight solids can behave similarly to entrained gas as described herein.

Preferred lightweight solids are those which include substantial quantities of trapped air or other gas. Those which are most preferred will be substantially impermeable to liquids such that areas occupied by trapped air or other gas will resist invasion by the surrounding liquids. Lightweight fillers that readily absorbed liquids or gels into its porous areas, may not provide the desired density reducing function over time. However it is perfectly acceptable for the lightweight filler to break apart during use, such as during brushing, since their desired bulkifying function has already been carried once it has been dispensed onto a toothbrush or other scrubbing medium.

Examples of lightweight, low density solid fillers include, but are not limited to, foamed polystyrene particles, foamed polypropylene spheres, foamed polymeric beads, expanded perlite, expanded vermiculite, hollow glass spheres, hollow aluminum oxide spheres, hollow ceramic spheres, hollow plastic spheres, lightweight expanded geologic materials, and the like. In the case of "open-cell" fillers such as expanded perlite, it will generally be desirable to treat such fillers with a sealer or coating in order to prevent substantial absorption of surrounding liquids or gels when used in toothpastes. Nonporous fillers such as hollow glass spheres are preferred due to their impermeability to liquids and gels. In addition, larger but more rounded fillers provide excellent cleaning of plaque while being less abrasive and prone to scratch tooth enamel. More spherical fillers also provide for more stable foams in the event that it is desired to incorporate both entrained gas and a lightweight filler.

In addition to adding bulk and greatly reducing the density of the dental composition, the lower density solid filler can be selected to optionally impart an abrasive action such that it can assist the other abrasives included within the dental composition. The only limitation is that the lightweight solid filler should substantially reduce the density of the toothpaste but also be safe when placed within the oral cavity of a human.

In light of the foregoing, it is an object of the present invention to provide compositions and methods for manufacturing toothpastes and other dentifrices which reduce the amount of fluoride and other active ingredients that might be ingested by adults or children while still providing their beneficial effects.

It is a further object of the present invention to provide compositions and methods for manufacturing toothpastes and other dentifrices that provide the desired concentration of active fluoride and other dental agents while reducing the amount delivered by the dentifrice.

In addition, it is an object of the present invention to provide compositions and methods to provide manufacturing toothpaste and other dentifrices that yield compositions having an increased rate of dispersion of fluoride and/or other active ingredients into saliva or water within a person's mouth compared to conventional toothpastes.

It is a further object of the present invention to provide compositions and methods for manufacturing and other dentifrices that have increased solubility and dispersibility in saliva such that the active dental agent, such as fluoride, is more rapidly available to effect its beneficial action.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

I. Introduction

The present invention relates to compositions and methods for creating expanded, lightweight toothpastes and other dentifrices in order to reduce the density of the toothpaste, or mass per unit volume. The benefit of doing this is at least twofold. First, reduced density toothpastes allow a person to dispense what appears to be a generous, full-bodied quantity of toothpaste onto the toothbrush as desired while reducing the actual quantity or mass of toothpaste being dispensed. This, in turn, reduces the quantity of active ingredients that might accidentally be ingested. Second, toothpastes which incorporate substantial void spaces increase the dispersibility of the toothpaste or other dentifrices in saliva or other aqueous systems, which accelerates or increases the availability of the active dental agents, particularly the uptake of fluorides. In other words the inventive dental compositions may at the same time provide increased effectiveness while lowering the risk of accidental poisoning by the active ingredients.

Fluorides and other medicaments are very useful in preventing tooth decay and treating other dental or oral ailments. The active ingredients in toothpaste and other dentifrices are usually safe when applied topically to tooth surfaces and/or gums. Medicaments found in toothpastes generally have little or no utility if ingested and can be harmful or even fatal if ingested in great enough quantities. This is particularly true in the case of children, who are generally much more sensitive to toxic doses of fluoride or other medicaments, or medicaments in which the threshold level of toxicity is far less in children due to their greatly smaller size and body weight compared to adults. By way of comparison, an adult weighing six times more than a child would have to ingest roughly six times more of a toxin in order for the toxin to have the same level of harm or toxicity.

In addition, whereas an adult has already gone through the growth stage, a child is still in the early stages of bodily development, which can create a whole array of developmental problems not experienced by adults. For example, in the early developmental stages of a child's teeth, particularly when baby teeth are replaced by permanent teeth, excessive fluoride, even if ingested in non-lethal amounts, can cause severe staining and mottling of the teeth. Excessive fluoride can also cause bone dyscrasia and other abnormalities, as well as inappropriate development of the teeth in general. For this reason, there has been growing concern that children should reduce the amount of fluoride intake in order to avoid the foregoing problems.

The reduction of fluoride in children has been problematic for a number of reasons, some political rather than scientific. First, the Food and Drug Administration of the United States has mandated that, in order to make the claim that a toothpaste contains fluoride, a manufacturer must include the mandated concentration range of fluoride, as measured in parts per million (between 950 ppm and 1150 ppm). By law "fluoride toothpastes" must include fluoride within the mandated range, regardless of whether the toothpaste is intended for adults or children. Therefore, toothpaste formulations for children are required by the government to have the same concentration of fluoride as adult compositions, notwithstanding the increased danger to children of such fluoride concentrations.

Instead of including lessor quantities of fluoride, the only identifiable difference between children's toothpaste and toothpastes made for adults is that children's toothpastes taste better. Some adult toothpastes often include unpleasant tasting ingredients, such as baking soda, tartar removing agents, plaque removing agents, and other medicaments. In contrast, to promote brushing children's toothpaste are often manufactured to taste as delicious as possible. Unfortunately, better tasting toothpastes may also encourage a young child to swallow the toothpaste while brushing, or worse yet, eat the toothpaste even while not brushing. As a result, children on average ingest far more toothpaste than adults, the harm of which is further multiplied by the child's greatly reduced body weight. The potential risk is severe tooth maldevelopment, discoloration, and mottling of enamel, and in some cases, even death.

Although toothpaste manufactures now recommend that children only use a "pea-size" quantity of toothpaste on the brush, such warnings are unheeded by children who either cannot read or do not fully comprehend or appreciate the risks associated with ingesting toothpaste. Moreover, children are bombarded by television and print advertisements showing a generous, full-bodied strip of toothpaste across the entire length of the toothbrush bristles. Common experience has shown that children tend to be far more vulnerable to media campaigns than adults, and the mental impressions formed by seeing a large, full-bodied amount of toothpaste are far more powerful and persuasive than recommendations to use a pea-size quantity.

In light of this, the inventors have developed compositions and methods for manufacturing toothpastes that greatly reduce the actual quantity of fluoride or other medicaments that enter a person's mouth by way of toothpastes or other dentifrices, while giving the person the illusion of receiving a large quantity by allowing the person to dispense a full-bodied, solid strip of toothpaste across the toothbrush. Hence, a person can have the satisfaction of feeling like he or she has used a large, even wasteful, amount of toothpaste, while in reality the actual mass of toothpaste has been substantially reduced such that the person ends up using the recommended quantity. In addition, reducing the density of the toothpaste allows for the delivery of less actual fluoride or other active ingredient while maintaining the mandated or desired concentration of that ingredient.

Figures 1, 2, 3:
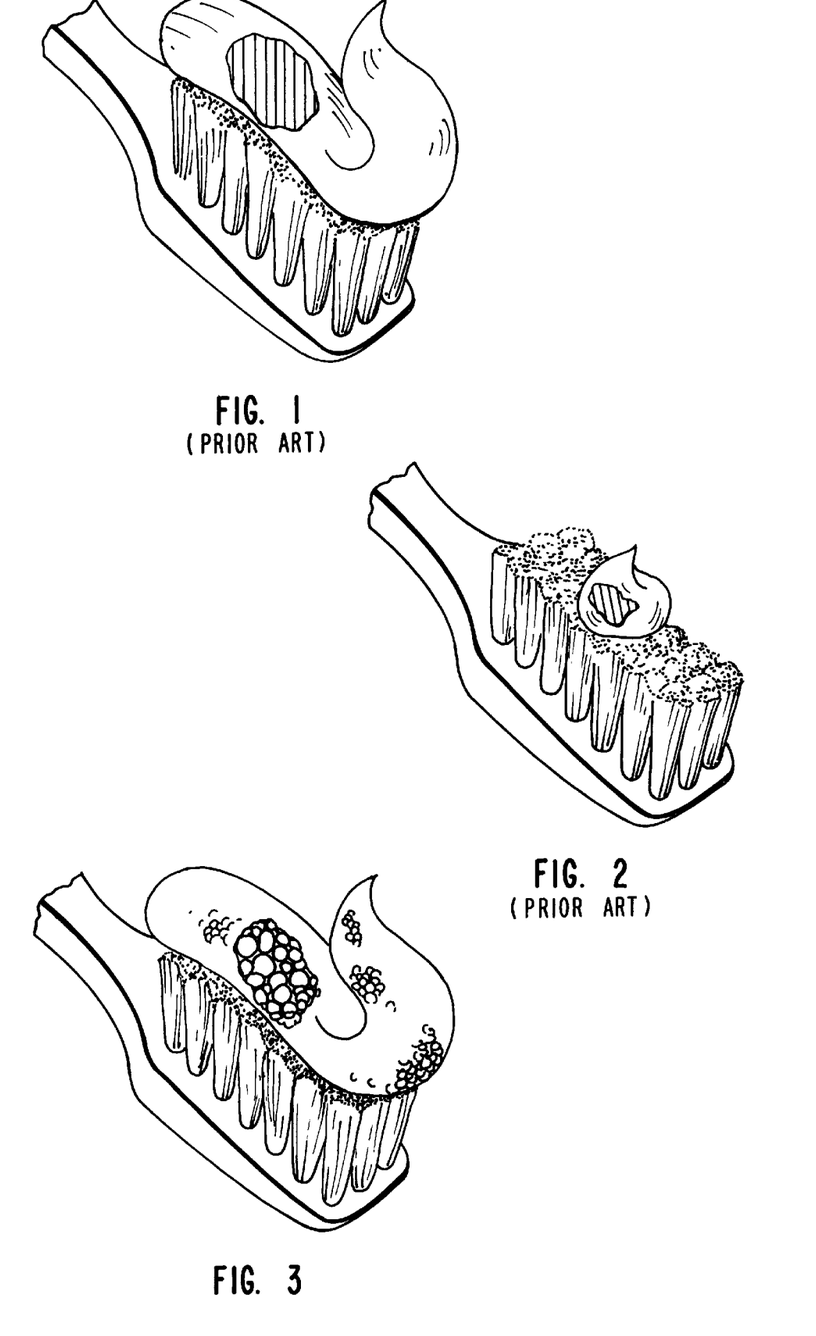
FIG. 1 is a perspective view of the end of a toothbrush having a solid strip of a conventional toothpaste and showing a breakaway section of the toothpaste.
FIG. 2 is a perspective view of the end of a toothbrush having a "pea-size" amount of toothpaste.
FIG. 3 is a perspective view of the end of a toothbrush having a solid strip of a foamed toothpaste of the present invention and showing a breakaway section of the toothpaste.

In order to illustrate the utility of the invention, reference is now made to the drawings. FIG. 1 shows a solid, full-bodied quantity of a conventional toothpaste spread across the length of a standard adult toothbrush, with a swirled wrap-around portion of toothpaste as a cute accent on one side. Manufacturers have conditioned the public to believe that the toothpaste depicted in FIG. 1 is the satisfying and desired amount. FIG. 1 also includes a break-away section of the toothpaste showing the interior of the toothpaste, which can be seen to be a solid mass of gel or paste with no density reducing component. In reality, the quantity of toothpaste depicted in FIG. 1 is far greater than what is necessary to actually clean the teeth and provide adequate fluoride treatment.

In fact, common experience shows that when relatively large quantities of toothpaste are used, much of it is wasted by either falling from the person's mouth into the sink or by not being adequately dispersed throughout the person's saliva. In any event, because cleansing and fluoride treatment of teeth is largely a surface reaction, any toothpaste not directly in contact with the surface of the teeth is largely wasted and should be considered excessive. Moreover, in the case of young children or mentally disabled adults, excess toothpaste may often be ingested, either accidentally or intentionally. Thus, using the amount of toothpaste depicted in FIG. 1 is not only wasteful but potentially harmful.

FIG. 2 depicts a "pea-size" amount of a conventional toothpaste on the toothbrush, which is adequate for most people, not just children. Not only is this the recommended quantity for young children, it is also a realistic amount of toothpaste that will adequately cleanse an adult's teeth and provide sufficient fluoride treatment. Notwithstanding this, one has rarely if ever encountered a television or print ad showing a pea-size quantity of toothpaste on a toothbrush. The result is that people have been conditioned to feel a sense of deprivation if only a pea-size amount were used.

By way of comparison, the quantity of toothpaste required to cover a typically-sized adult toothbrush illustrated by FIG. 1 weights about 2.4 g, while the "pea-sized" amount illustrated by FIG. 2 weighs approximately 0.8 g. Thus, the pea-size amount recommended by children's toothpaste manufacturers is about ⅓ the size of the amount depicted in FIG. 1. The amount of fluoride delivered into a person's mouth by the amount illustrated by FIG. 1 is about 0.0026 g, while the amount within the pea-sized quantity illustrated by FIG. 2 is only about 0.00088 g, which is ⅓ as much.

FIG. 3 shows a large, full-bodied strip of a low density toothpaste made according to the present invention on top of an adult tooth brush. The lower density results from trapped air, either by way of direct air entrainment or by means of air or other gases encapsulated within a low density filler. By way of comparison, assuming that the amount of toothpaste depicted in FIG. 2 is ⅓ the size of the toothpaste depicted in FIG. 3, and also assuming that the toothpaste in FIG. 3 has only ⅓ the density of the toothpaste depicted in FIG. 2, the actual quantity or mass of the two toothpaste amounts depicted in FIGS. 2 and 3 is the same. On the other hand, the actual quantity of toothpaste depicted in FIG. 1 is three times the amount shown in FIG. 3, although they look the same. (Of course, FIG. 3 is merely illustrative of one embodiment in which the normal density of the toothpaste has been reduced by about ⅔. It should not be construed as in any way being limiting of the present invention.)

This clearly and succinctly demonstrates the beauty of the invention: the very satisfying and generous amount of toothpaste depicted in FIG. 3 looks the same as the amount in FIG. 1 but is, in actuality, the same as the pea-size amount depicted in FIG. 2. The result is that children and adults can be, in effect, fooled into thinking they are getting a standard quantity of toothpaste while, in reality, they are being limited to the equivalent of a pea-sized amount. Moreover, because only the density has been reduced, the toothpaste of FIG. 3 can have the same concentration of fluoride as the toothpastes of FIGS. 1 and 2, thus satisfying the demands of the FDA for fluoride toothpastes. The result is that a person gets to use "more" of a fluoride toothpaste having the mandated concentration of fluoride, while actually receiving a more limited actual quantity of fluoride that might be ingested.

If the only effect of entraining air were to reduce the risk of fluorosis and other ailments that can result from ingestion of fluoride and other medicaments in toothpastes and other dentifrices, then the dental compositions of the present invention would have great utility. Nevertheless, the inventors have found that foaming the dental compositions often increases the dispersibility and, hence, the availability of the active ingredients in the dentifrice, sometimes dramatically. It is postulated that this is due to the enhanced ability of foamed toothpastes or other dentifrices to dissolve or disperse within saliva and water such that the active medicaments, such as fluoride, are more quickly dissolved into the person's saliva and then dispersed over the tooth surfaces being treated.

One possible reason for this is that foamed toothpastes having entrained air or air pockets have a greatly increased effective surface area, which greatly increases the interface area between the toothpaste and saliva or water. This, in turn, can increase the solvating action of the saliva and/or water. The result is greater availability and uptake of fluoride and other medicaments, even though the actual amount of such medicaments has been reduced as a result of providing a lower density dentifrice. The result is greater efficiency per unit mass of the active ingredient. Because most people on average brush for 60 seconds or less, it is important that the fluoride or other active ingredients be rapidly deployed over the surface of the person's teeth. Otherwise, their intended benefit may not be realized to the extent desired.

The same or similar effect can be provided by certain lightweight fillers, such as hollow glass spheres, which can break apart and release tiny gas bubbles into the toothpaste during vigorous brushing in some cases. In addition, such fillers can provide enhanced cleaning of soft dental tissues and provide more plaque-cleaning power while, at the same time, being more gentle and less abrasive on the tooth enamel.

II. Constituents Within the Inventive Dental Compositions

In order to manufacture dentifrice compositions of reduced density and increased bulk, the inventors have identified a number of components which aid in the formation of the inventive dentifrices and the stabilization of the air entrainment if necessary. It should be understood that virtually any toothpaste in the market or known in the art can be modified so that it includes substantial quantities of entrained or trapped air or other gases in order to create the aforementioned benefits of foamed toothpaste. Therefore, while the present application discusses certain preferred methods and/or additives that facilitate the formation of toothpastes of reduced density, it should be understood that any conventional toothpaste known in the art that incorporates substantial quantities of entrained or trapped gas or air such that a toothpaste of greatly reduced mass can be dispensed onto the user's toothbrush will be within the scope of the present invention. An example of unfoamed and unexpanded toothpaste compositions known in the art is set forth in U.S. Pat. No. 3,988,433 to Benedict, as well as those commonly sold in the market, which have heretofore been incorporated by reference for purposes of disclosure.

A. Base Composition

The portion of the dental composition exclusive of the density reducing means or density reducing component comprises the "base composition". In other words, the "base composition" is that portion of the overall dental composition besides the density reducing means. In the case where the density reducing means comprises a gas, the base composition will supply essentially all of the mass or weight of the final dental composition, since the gas provides an insignificant quantity of mass or weight. In the case where the density reducing means includes or consists of a low density solid filler, the filler will provide a much lower percentage of the mass or weight compared to the base composition. The base composition comprises one or more dental agents dispersed within a carrier. In the case of a dental composition used to clean teeth, the base composition will preferably include an abrasive to assist in cleaning the person's teeth.

1. Dental Agents

The primary dental agent found in virtually all toothpastes is fluoride, which is an anticarious compound used to prevent tooth decay. Although very beneficial if used in appropriate quantities, fluoride can become dangerous if ingested in significant quantities. Examples of fluoride compounds useful as a decay prevention agent include, but are not limited to, sodium fluoride, potassium fluoride, calcium fluoride, magnesium fluoride, sodium fluorosilicate, stannous fluoride, stannous monofluorophosphate, sodium monofluorophosphate, and copper fluoride. Each of the foregoing fluoride compounds comprises a "fluoride ion source". A more complete discussion of fluoride compounds useful in fighting cavities may be found in U.S. Pat. No. 3,535.421 to Briner et al. For purposes of disclosure, the foregoing patent is incorporated herein by specific reference.

In order to deliver an effective amount of fluoride to a person's teeth, the foamed dental compositions of the present invention will include a fluoride concentration such that the fluoride ions are included in a range from about 10 ppm to about 3500 ppm, more preferably in a range from about 850 ppm to about 1150 ppm of fluoride ions. The exact amount of fluoride will depend on the solubility and dispersibility of fluoride and also FDA guidelines for fluoride-containing toothpaste. The FDA presently requires "fluoride toothpastes" to include at least 900 ppm of available fluoride ions.

Other dental agents or medicaments that can be included instead of, or in addition to, fluoride include antimicrobial agents that can be added to fight gum and periodontal diseases and desensitizing agents. Examples of antimicrobial agents include, but are not limited to chlorhexidine, tetracycline, cetyl pyridinium chloride, benzalkonium chloride, cetyl pyridinium bromide, methylbenzoate, propylbenzoate, and peroxides. Examples of desensitizing agents include, but are not limited to, potassium nitrate, citric acid, citric acid salts, strontium chloride, and the like.

2. Carrier

In order to deliver the appropriate concentration of dental agent to the user, the dental agent should be dispersed within a flowable substance that will allow for the dental agent to be dispensed onto e.g., a toothbrush. Because any toothpaste or dentifrice known in the art can be modified to include substantial quantities of entrained air or gas, the appropriate carrier could be any substance known in the art that has been found useful as a carrier in manufacturing toothpaste and tooth gels known in the art.

The term "carrier", as used herein, is defined as one or more compatible components which dilute and deliver the dental agent in appropriate quantities in an appropriate manner. Hence, appropriate carriers may include solid, liquid, gel-like, and gaseous components. Such components should be "compatible", which means that they are capable of being used together in a foamed composition without destabilizing or otherwise adversely affecting the foamed nature of the dental composition so that it will behave in the desired manner.

Examples of components found in carriers within conventional toothpastes are set forth in U.S. Pat. No. 3,988,433 to Benedict, the disclosure of which is incorporated herein by reference. Although Benedict may not necessarily use the term "carrier" to define the components found therein, any component other than the dental agent or medicament found in the composition of Benedict may fairly be referred to as a "carrier" component.

Materials that are used as carriers may also be used for other purposes in a dentifrice composition, such as acting as a humectant, abrasive, thickener, foaming agent, surfactant, and the like. Thus, although one of the components used in a toothpaste may be identified as providing a particular function, as used herein such other components will normally be classified under the rubric of being a "carrier" so long as it in some way aids in the delivery of an appropriate concentration of fluoride or other dental agent.

Carriers typically include a water-soluble gel or other material that gives bulk and the desired flow properties to the dental composition. Typically, a thickener or gelling material is dispersed in water or other solvent such as glycerine or polyethylene glycol to yield a carrier safe for use inside a person's mouth.

In order to protect the teeth and other oral tissues of the user, it will be preferable for the carrier to have a ph in a range from about 5 to about 9, more preferably in a range from about 6 to about 8. Examples of buffers and bases that can be used to adjust the pH include citrate, citrate-bicarbonate, and phosphate buffers, sodium hydroxide and amines.

3. Thickening Agents

A common constituent within a carrier will be a thickening, material, which may be used to provide bulk and a suitable consistency. Thickeners may be especially important in foamed dentifrice compositions since they may assist in stabilizing the entrained gas. They also may help keep the foamed composition firm and from having a liquid consistency. Hence, in a preferred embodiment, the foamed dentifrice compositions of the present invention will include a thickener as part of the carrier.

Appropriate thickeners may include either inorganic organic thickeners, or both. Inorganic thickeners that may be included in the dentifrice and toothpaste compositions of the present invention include fumed silicas dispersed in water, such as Cab-o-sil available from Cabot Corporation, and thickening silicas, including those available from W. R. Girace designated as Sylox 15.

Appropriate organic thickeners include natural and synthetic gums and colloids. Examples of organic thickeners include carrageenan (derived from Irish moss), xanthan gum, guar gum, other polysaccharide gums, sodium carboxymethyl cellulose, starch, polyvinyl-pyrrolidone, hydroxyethylpropylcellulose, hydroxybutylmethylcellulose, hydroxypropyl-methylcellulose, hydroxyethylcellulose, other cellulosic ethers, and carboxypolymethylene. Such materials are typically dispersed in water and/or other solvents, such as glycerine or polyethylene glycol.

Thickening materials will preferably be incorporated in the compositions of the present invention in a concentration in a range from about 0.05% to about 25% by weight of the composition, and preferably in a range from about 0.1% to about 10% by weight.

4. Abrasives and Polishes

The carrier will typically include one or more abrasive materials to help clean and polish the teeth. Because solids are inexpensive and can add bulk, they will normally comprise a substantial fraction of the carrier. Almost any granular solid or powder can act as an abrasive or polish, although certain solids are preferred in order to clean, yet avoid scratching, the tooth enamel. Conventional abrasives typically include salts having anti-tartar activity and which include, but are not limited to, dicalcium orthophosphate, calcium carbonate, silica and silicates beta-phase calcium pyrophosphate, sodium metaphosphate, long chain polyphosphates such as sodium hexametaphosphate and cyclic phosphates such as sodium trimetaphosphate as well as alkylmetatripolyphosphates such as sodium tripolyphosphate and potassium tripolyphosphate.

Mixtures of abrasives can also be used. The total amount of abrasive in the dentifrice of the present invention will preferably be in a range from about 0.5% to about 95% by weight of the dentifrice, and more preferably in a range from about 20% to about 60% by weight of the dentifrice. The abrasive and polish components should be distinguished from the optional lightweight filler components since conventional abrasives and polishes usually have a density greater than about 1 g/cm$^3$. Thus, the term "abrasive" shall be construed to constitute an abrasive component other than a lightweight filler even though the lightweight filler may itself import abrasive activity. The term "abrasive" also includes polishes, which are generally very fine abrasives.

Polishing agents may be included in dentifrice compositions that contain siliceous materials, such as silica, which have a mean particle size up to about 10 microns and a very high surface area, e.g. in the range of 150–750 square meters/gram. Polishing agents differ from abrasives mainly in the former having a smaller particle size. A preferred polishing agent is a precipitated amorphous hydrated silica, such as Sorbosil AC-35 marketed by Crosfield Chemicals. Other polishing agents may also be employed, including peroxide reactive polishing agents such as sodium bicarbonate, calcium carbonate, as well as sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina, and bentonite.

When polishing agents are present in the dentifrice composition of the present invention, they are preferably included in a range from about 10% to about 30% by weight of the dental composition, more preferably in a range from about 5% to about 25% by weight.

5. Foaming and Stabilizing Agents

Foaming and stabilizing agents are typically included in prefoamed dental compositions, and aid in both entraining the gas to form the foam, and also assist in stabilizing the foam in many cases. As used in the present invention, the term "foaming agent" is defined as any substance that aids, or otherwise helps, the dentifrice composition become foamed or be maintained in a foamed state. Foaming agents generally work in conjunction with mechanical foaming devices, such as high speed mixing devices.

In order for pre-foamed dentifrice compositions to have a commercially practical shelf-life, the foamed compositions need to be shelf stable as a foam for prolonged periods of time and subsequently be ready for application. Stabilized foaming agents within the scope of the present invention should be non-toxic and should not contribute to the formation of carries. There are many foaming and stabilizing agents known that are capable of safely and effectively stabilizing foamed dentifrice compositions including, but are not limited to, soaps, proteins, extract of licorice root, fatty acids, and sulfite liquids.

6. Surfactants

Surfactants may be included in order to aid in dispersing the dentifrice composition throughout the oral cavity and also as a cleansing agent. They also may act as a foaming agent as discussed above. Surfactants help disperse the toothpaste within water and saliva found in the mouth during brushing. Surfactants may also improve the cosmetic acceptability and foaming properties of the dentifrice in the oral cavity.

Among the organic surfactants useful in the practice of the present invention are salts of the higher alkyl sulfates, such as sodium lauryl sulfate (SLS) or suitable alkyl sulfates having 8 to 18 carbon atoms in the alkyl group; sodium lauryl sulfoacetate, salts of sulfonated monoglycerides of higher fatty acids, such as sodium coconut monoglyceride, sulfonate or other suitable sulfonated monoglycerides of fatty acids of 10 to 18 carbons; salts of amides of high fatty acids. e.g.. 12 to 16 carbon atoms, with lower aliphatic amino acids, such as sodium-N-methyl-N-palmitoyl taurides sodium N-lauroyl-, N-myristoyl- and N-palmitoyl sarcosinates; salts of esters of fatty acids with isothionic acid or with glycerol monosulfate, such as the sodium salt of monosulfated monoglyceride of hydrogenated coconut oil fatty acids; salts of olefin sulfonates, e.g., alkene sulfonates or hydroxyalkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt is typically sodium, potassium or mono-, di- or triethanolamine.

Mixtures of two or more surfactants can be used if desired to obtain desired properties. Additional useful surfactants may include the non-ionic, cationic, zwitterionic, amphoteric non-soap organic synthetic detergents. A full range of suitable surfactants is disclosed in U.S. Pat. No. 3,988.433 issued to Benedict, the disclosure of which has been incorporated herein by reference.

Surfactants are preferably included in the dentifrice of the present invention is at a concentration in a range from about 0.5% to about 3% by weight, and more preferably from about 1% to about 2% by weight.

7. Humectants

It may be desirable to include a humectant material in a dentifrice or toothpaste composition in order to maintain moisture in the composition and keep the composition from becoming excessively stiff or hardened. Suitable humectants include, but are not limited to glycerin, sorbitol, and other polyhydric alcohols that are suitable for human consumption. The humectant may be included in an amount up to about 40% by weight of the dentifrice composition. Alternatively, the dentifrice composition may contain up to about 40% by weight of a paraffin oil as a non-humectant softening agent.

8. Miscellaneous Components

Various other miscellaneous materials and components may be incorporated into the dentifrice composition of the present invention. Non-limiting examples of these various components include solid lightweight fillers, polishing agents, peroxides, colorants, dyes, flavoring and sweeteners.

Bicarbonate compounds, when included in the dentifrice components of the present invention as a cleansing or refreshening agent, are present at a concentration in a range from about 5% to about 20% by weight, and preferably in a range from about 8% to about 15% by weight. The particle size of the bicarbonate compounds can range from about 10 to about 300 microns. A particle size of about 20–60 microns is preferred, although the smaller particle size bicarbonate compounds can be more readily dispersed in the dentifrice carrier.

Peroxide compounds may be used as an ingredient in the dentifrice and toothpaste compositions of the present invention as a cleansing or whitening agent. When peroxide compounds are present in the dentifrice composition, the peroxide compounds are preferably included in a range from about 0.25% to about 5% by weight of the dentifrice composition, more preferably in a range from about 0.5% to about 2.0% by weight. Peroxide compounds suitable for use with the dentifrice and toothpaste compositions of the present invention include metal peroxides such as calcium peroxide, magnesium peroxide, and zinc peroxide.

Colorants such as pigments and dyes may be used in the practice of the present invention. Pigments include non-toxic water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake. FD&C #30 lake and FD&C # Yellow 15 lake. The pigments have a particle size in a range of about 0.1–500 microns, preferably about 0.1–50 microns, and are preferably included in a concentration of about 0.5% to about 3% by weight.

Dyes used in the practice of the present invention are generally food color additives presently certified under the Food Drug and Cosmetic Act for use in food and ingested drugs, including dyes such as FD&C Yellow No. 5 (sodium salt of 4-p-sulfophenylazo-1-p-sulfophenyl-5- hydroxypyrazole-3 carboxylic acid), FD&C Yellow No. 6 (sodium salt of p-sulfophenylazo-B-naphthol-6-monosulfonate), FD&C Green No. 3 (disodium salt of 4-{4-(N-ethyl-p-sulfobenzylamino)-phenyl]-(4-hydroxy-2-sulfoniumphenyl)methylene}-[1-(N-ethyl-N-p-sulfobenzyl)-δ-3,5-cyclohexanediamine], FD&C Blue No. 1 (disodium salt of dibenzyldiethyldiaminotriphenylcarbinol trisulfonic acid anhydride), FD&C Blue No. 2 (sodium salt of disulfonic acid of indigotin) and mixtures thereof in various proportions. The preferred concentration of dye for the most effective result, when dyes are used in the present invention, is in an amount in a range from about 0.05% to about 10% by weight of the dentifrice compositions, and preferably from about 0.5% to about 2% of the total weight of the dentifrice composition.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon, lemon, orange, and methyl salicylate. Suitable sweetening agents include sucrose, lactose, maltose, sorbitol, sodium cyclamate, perillartine, and sodium saccharin. Suitable flavor and sweetening agents may together comprise from about 0.01% to about 5% of the dentifrice compositions.

Various other materials may be incorporated into the dentifrice composition of this invention. Non-limiting examples thereof include preservatives, silicones and chlorophyll compounds, antibacterial agents such as chlorhexidine, halogenated diphenyl ethers such as Triclosan, desensitizing agents such as potassium nitrate and potassium citrate and mixtures thereof. These adjuvants are incorporated in the dentifrice composition in amounts which do not substantially adversely affect the properties and characteristics desired, and are selected and used in proper amounts, depending upon the particular type of dentifrice component involved.

B. Density-Reducing Means

The terms "density-reducing means" and "density-reducing component" shall include entrained gas and/or lightweight filler components. In general, the density reducing means shall comprise the constituent that is primarily added to the base composition in order to reduce the density and increase the bulk and volume of the final dental composition. It should be understood that reducing the density is the same as increasing the volume and bulk per unit weight. In this way, the volume of the dental composition can be significantly or greatly increased by the density reducing means in order to allow a larger volume of the dental composition to be introduced onto a toothbrush, while reducing the actual amount of fluoride and other active ingredients actually delivered into a person's mouth.

In a first embodiment, the density reducing means will comprise entrained air or other gas. Entraining gas yields a final composition in which the final concentration of the fluoride or other active ingredient remains essentially the same as before the gas was added to the base composition. Moreover, gases are versatile because they may be readily entrained within dental compositions during manufacture or in situ at the time of use. Gases also tend to be inert and nonreactive vis-a-vis the active ingredients.

In conjunction with or at least partially in lieu of, the entrained gas, the density reducing means may include a solid, lightweight filler. The solid lightweight filler can be used to greatly decrease the density of the inventive dental compositions and provide lightweight bulk therein. A solid lightweight filler is defined as a material having a relatively low density or specific gravity, preferably less than about 0.5 g/cm$^3$, more preferably less than about 0.3 g/cm$^3$, and most preferably less than about 0.1 g/cm$^3$. Because lightweight fillers can act to displace a substantial portion of the active dentifrice without substantially reducing the weight percent of the active dental agent, lightweight solids can behave similarly to entrained gas, as described herein.

Solid, low density fillers may be organic or inorganic. Examples of lightweight inorganic fillers include hollow glass spheres, hollow aluminum oxide spheres, hollow ceramic spheres, expanded perlite, expanded vermiculite, acrogels, expanded silica gels, lightweight expanded geologic materials, and the like. The term "hollow glass spheres" broadly encompasses spheres made from any known glass or glass-like substances, including but not limited to, silicon dioxides, soda-lime-borosilicates, aluminum oxides, silica-alumina ceramic glasses, and alkali-alumina-silicate ceramic glasses. Examples of lightweight organic fillers include cork, polystyrene foam particles, polyethylene particles, polypropylene particles, hollow plastic spheres, and other low density and/or expanded polymeric materials.

In the case of "open-cell" fillers such as expanded perlite, it will generally be desirable to treat such fillers with a sealer or coating in order to prevent substantial absorption of surrounding liquids or gels when used in toothpastes or other dentifrices. Nonporous fillers such as hollow glass spheres are preferred due to their impermeability to liquids and gels. In addition, relatively large diameter rounded fillers (e.g., having a diameter in a range from about 20–150 microns) provide excellent cleaning of plaque while being less prone to scratch tooth enamel. More spherical fillers also provide far more stable foams in the event that it is desired to incorporate both entrained gas and a lightweight filler together within the lightweight dental compositions of the present invention.

A presently preferred hollow glass bubble or sphere useful in forming the expanded dental compositions of the present invention is available from 3M and sold as K1 series Scotchlite Glass Bubbles. These glass bubbles are made from soda-lime-borosilicate glass, have a target crush strength (90% survival) of 250 psi, and have a true density of 0.125 g/cc. The bubble size ranges from about 20 to about 120 microns, with the 50th percentile of size distribution being 65 microns.

In terms of particle size, such hollow glass bubbles are substantially larger than conventional abrasives used in toothpastes. Because conventional abrasives are generally quite jagged and abrasive, they are milled to much smaller sizes (usually less than 20 microns) in order to reduce their tendency to abrade teeth. Surprisingly, the much larger sized glass bubbles (e.g., 20–150 microns in diameter), while providing little if any abrasive power for cleaning stains from enamel due to their spherical shape and larger size, have been found to be particularly effective in removing plaque from teeth and soft tissues such as gums. Thus, toothpastes that include significant quantities of hollow glass spheres, or any type of large, spheroidal or otherwise round-edged filler, will provide enhanced plaque-removal capability while being generally less abrasive to enamel compared to conventional abrasives and polishes found in toothpastes.

Other hollow glass bubbles having varying compositions, crush strengths, densities and particle size distributions would also provide the aforementioned plaque-cleaning properties. In fact, virtually any round-edged, non-jagged particle would be less abrasive, although those having a relatively-large diameter (i.e., from about 10 to 150 microns) will be particularly effective in cleaning plaque from teeth and soft tissues.

The density reducing means are preferably included in an amount in a range from about 25% to about 90% by volume, more preferably greater than about 30% by volume, and most preferably greater than about 50% by volume.

III. Preparation of the Inventive Dental Compositions

The dentifrice and toothpaste compositions which are either foamed or which include a lightweight filler can be prepared using conventional techniques known in the art. For example, the dentifrice or toothpaste compositions can be prepared by blending each of the solid ingredients into a liquid carrier component, i.e., polyalkylene glycol, which is normally viscous at room temperature. Conventional adjuvants can then be included.

Once the desired dentifrice or toothpaste composition is formed, the composition can be foamed to form a foamed dentifrice or toothpaste composition within the scope of the present invention. Foam is produced in dentifrice or toothpaste compositions by introducing air or a gas into the toothpaste or dentifrice composition. Examples of foaming dentifrice or toothpaste compositions include foaming by mechanical means or chemical means. Alternatively, gas can be incorporated into the dental composition, which is then stored in compressed form under pressure. Upon dispensing the composition, the compressed gas will develop foam within the toothpaste upon being exposed to atmospheric pressure.

In one embodiment, the dentifrice composition is foamed prior to packaging (referred to as pre-foamed). When the dentifrice composition is foamed and then packaged, the dentifrice composition preferably comprises a foam stabilizing agent so that the foamed dentifrice composition is shelf-stable for a commercially practical period of time. The dentifrice composition is preferably foamed using mechanical means, such as high speed mixing or other agitation. The foamed composition is then placed into a suitable container, such as a conventional toothpaste tube or pump container for storage. The inventive compositions should be stable as a foam: i) after mixing; ii) after storage of the composition for extended periods of time; and iii) after delivering a portion of the foamed composition from the container. Hence, upon opening and using a portion of the foamed toothpaste, the remaining foamed toothpaste can be resealed and reused while remaining as a stable foamed composition.

In another embodiment of the present invention, chemical foaming agents are used to foam the dentifrice composition prior to packaging. Chemical foaming agents create foam or entrained gas when the foaming chemicals are mixed together. An example of chemical foaming is the formation of carbon dioxide from the chemical reaction of aluminum sulfate and sodium bicarbonate. As with mechanical foaming, a foam stabilizer is preferably included with the chemically foamed dentifrice compositions in order to stabilize the foamed composition during storage, use and reuse.

In still another embodiment, the dentifrice composition may constitute a pressurized foaming composition. As used in the present invention, the term "pressurized foaming composition" is defined as a suspension of compressed gas voids within a liquid. A common example of a pressurized foaming composition is conventional shaving cream, wherein a gas is compressed in a container and upon release, a foamed material is produced. In correction with the present invention, the dentifrice composition is formed using conventional methods as discussed above. The dentifrice composition is then placed in a container with a suitable compressed gas, under pressure, using conventional compression techniques known in the art. Subsequently, when the dentifrice composition is dispensed from the container, the pressure of the gas causes the dentifrice composition to be dispensed as a foamed dentifrice composition. An example of a suitable propellant and foaming agent is carbon dioxide gas.

Alternatively, the dentifrices can be placed into a container under pressure along with foaming agents that will cause the dentifrice to foam upon being dispensed from the container and being exposed to the atmosphere. Similarly, a container of toothpaste can be provided in conjunction with a separate compartment of compressed gas, which gas can mix with the toothpaste during the dispensing process in order to foam the toothpaste at the time of use.

In yet another embodiment, air can be entrained into the initially unfoamed dental composition by means of the pumping action required to express the dental composition from the container within which it is stored.

Finally, some or all of the entrained air can be replaced with an appropriate low density, lightweight filler such as hollow glass spheres, hollow ceramic spheres, hollow and other low density plastic spheres, expanded geologic materials such as perlite which have been sealed to prevent substantial absorption of liquids, and the like. These fillers are typically blended with the other components using low shear mixing in order to avoid breaking such fillers. Air and other gases can be entrained along with the lightweight fillers according to any appropriate method set forth above.

IV. Characteristics of the Inventive Dental Compositions

In order for the inventive expanded dental compositions to behave and seem like conventional toothpaste, the carrier should have a viscosity such that when substantial quantities of air and/or lightweight aggregates are entrained or mixed therein, the toothpaste will have a viscosity, yield stress, and other rheological properties such that it will flow from the storage container (e.g. a squeeze tube or syringe) onto the toothbrush and substantially maintain itself as a bead or line of composition across the tooth bristles for at least a short period of time. If the composition is too runny or nonviscous, the foam might collapse such that material could fall between the bristles of the toothbrush and cause the user to use more of the composition than is intended. On the other hand, the material should not be so stiff and viscous that it cannot be easily expressed from the container without undue difficulty. In light of the disclosure set forth herein, one of ordinary skill in the art will know how to adjust the various components within the carrier material in order to obtain a stiffness and viscosity that will satisfy the aforementioned criteria.

Once the dental composition has been foamed, either during mixing to form a pre-foamed dental composition or in situ using compressed gas, the dental composition will include entrained gas or trapped air in a range from about 20% and about 90% by volume of the foamed composition, preferably greater than about 25% by volume, more preferably greater than about 30% by volume, and most preferably greater than about 50% by volume of the foamed toothpaste or dentifrice composition. The foregoing ranges are applicable when entrained air is the sole density reducing means.

The foregoing concentrations of entrained or trapped gas are measured at the time the dental composition is dispensed from the storage container onto a toothbrush or other applicator means. However, they do not constitute a limitation as to when foaming or expansion of the dental composition actually occurs. Though it might be said that the dental composition has a certain concentration of entrained gas "upon dispensing the dental composition from a storage container", it will be appreciated that the dental composition may either be pre-foamed or foamed in situ using, e.g., compressed gas.

In the event that a lightweight filler material is used in conjunction with, or in place of, entrained gas or air in order to reduce the density of the dental composition, the amount of lightweight filler will be such so as to maintain an appropriate rheology as described above. Moreover, the weight of the lightweight filler should be factored into the overall weight of the composition when determining the weight percent of the active dental agent. It may thus be necessary to increase the amount of the active ingredients by some degree to maintain the desired concentration due to the weight-increasing effect of the lightweight filler.

In order to achieve the benefits of the present invention, the lightweight filler material will be included within the composition, if included at all, in an amount such that the dental composition has a reduction in density, either alone or in combination with entrained air or other gas, in a range from about 20% to about 90% compared to the density of the "base composition" exclusive of the lightweight filler material. Preferably, the reduction in density will be greater than about 25% in comparison to the base composition exclusive of the lightweight filler. More preferably, the reduction in density will be greater than about 30% and, most preferably, greater than about 50% in comparison to the base composition exclusive of the lightweight filler. Either entrained air and/or lightweight filler will comprise means for reducing the density of the dental composition.

As can be seen, the reduction in density caused by the lightweight filler, alone or in combination with entrained air, corresponds to the preferred ranges of the volume of entrained gas within foamed dental compositions that do not include lightweight fillers. As such, when both entrained gas and lightweight filler material are incorporated, it can readily be seen that the combined reduction in the density of the dental composition will be approximately the same as where it is reduced simply by incorporating gas or air, which contributes no mass while contributing high volume. This is also true for where a lightweight aggregate is used exclusively to reduce the density of the composition.

Because there is a direct correlation between the reduction of density and the increase of the bulk and volume of the dental composition per unit weight, it may be helpful to understand how the reduction in density increases the volume of the dental compositions according to the invention. A 20% decrease in the density of the base composition roughly increase the volume per unit weight by about 25%, meaning that the final dental composition would have a volume that is 125% of the initial volume of the base composition. On the other hand, reducing the density by 90% would increase in the volume per unit weight of 900%, which means that the final dental composition would have a volume that is 1000% of the base composition. Likewise, a 25% decrease in the density constitutes a 33% increase of the initial volume such that the final volume is 33% of the initial volume of the base composition; a 33% decrease in the density yields a volume increase of about 50%; a 40% decrease in the density corresponds to a volume increase of about 67%; a 50% decrease in the density translates into a doubling of the volume, or an increase of 100%; and a decrease in density by 66.7% translates into a tripling of the volume, or an increase of 300%, which means that the final dental composition has 400% of the volume of the base composition, or 4 times the volume.

V. Examples of the Preferred Embodiments

The following examples are presented in order to mole specifically teach the preferred compositions and methods for forming and using low density dentifrices according to the present invention. The examples which have actually been made are written in past tense, while those that are merely hypothetical are written in present tense. Although some examples are hypothetical in nature, they are based on or derived from actual mix designs and conditions for making lower density dental compositions according to the present invention.

EXAMPLE 1

A base dental composition of normal density that was suitable for use in brushing or cleaning teeth was made by combining the following components:

| | |
|---|---|
| Distilled water | 21.6% |
| Glycerin | 25% |
| Sorbitol | 25.26% |
| Sodium Fluoride | 0.25% |
| Sodium Benzoate | 0.22% |
| Fumed Silica | 3% |
| Abrasive Silica | 19.5% |
| Aspartame | 0.22% |
| Surfactants | 2.6% |
| Xanthan gum | 0.46% |
| Carbomer | 0.3% |
| Flavors | 1.0% |
| FD&C Colorants | 0.59% |

The base dental composition had a density of 1.4 g/cm$^3$. Thereafter, the base dental composition was "spiked" with various quantities of hollow glass spheres in order to study the effect of adding a lightweight filler on the density of the resulting dental composition. The hollow glass spheres that were added were K1 series Scotchlite Glass Bubbles manufactured by 3M. These hollow glass spheres were made from soda-lime-borosilicate glass, had a target crush strength (90% survival) of 250 psi, and had a density of 0.125 g/cm$^3$. The size distribution of the hollow glass spheres ranged from about 20 to about 120 microns, with the 50th percentile of size distribution being 65 microns.

To 100 parts of the base composition were added the following quantities of K1 series Scotchlite Glass Bubbles, measured in terms of parts and percent by volume, to form various "filled compositions". The resulting densities of the filled compositions are also listed:

| Quantity Added | Volume Percent | Resulting Density |
|---|---|---|
| 0 parts | 0% | 1.4 g/cm$^3$ |
| 30 parts | 15% | 0.96 g/cm$^3$ |
| 50 parts | 25% | 0.93 g/cm$^3$ |
| 70 parts | 35% | 0.86 g/cm$^3$ |
| 100 parts | 50% | 0.81 g/cm$^3$ |

The above values were plotted and found to be essentially linear, meaning that there is an essentially linear relationship between the volume of added hollow glass spheres and the reduction in density within this concentration range. This is because of the tremendous disparity between the density of the base composition and that of the hollow glass spheres. Of course, since the hollow glass spheres do, in fact, add some additional weight to the dental composition, the relationship is not precisely linear, particularly at very high concentrations of hollow glass spheres (i.e. approaching 100% by volume).

The resulting filled dental compositions had a substantial reduction in density, which means that hollow glass spheres worked well in creating expanded, low density dental compositions that had greatly reduced mass per unit volume but which did not have substantially reduced concentrations of fluoride or other active ingredients.

The dental compositions having hollow glass spheres were tested to determine how well they cleaned teeth. Whereas the reduced density toothpastes were found to provide the same level of benefit with regard to the effects of fluoride treatment of teeth compared to conventional toothpastes, a surprising and unexpected benefit was increased plaque removal without any detectable increase in the abrasion of tooth enamel. It is believed that the increased size of the hollow glass spheres resulted in an enhanced ability of the dental composition to mechanically break up and disperse the plaque, thereby facilitating the dissolution and removal of plaque from the teeth and surrounding soft tissues by the solvents and surfactants present within the dental compositions. The rounded, non-jagged profile of the hollow glass spheres allowed for the aforementioned plaque removal without significant scratching of the enamel or irritation of the surrounding gums or gingival tissue.

EXAMPLE 2

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled water | 30% |
| Glycerin | 25% |
| Flavor and color | 1.5% |
| Mannitol | 15% |
| Sodium laurel sulfate | 2% |
| Xanthan gum | 1% |
| Abrasive silicon dioxide | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. By way of example, if 20% by volume of a gas is entrained within the base composition, the resulting composition will have a density that is essentially 80% of the density of the base composition, or a density reduction of essentially 20% compared to the base composition. Increasing the volume of gas that is entrained reduces the density of the resulting composition by a corresponding amount. Entraining 90% by volume air will reduce the density by 90%, resulting in a final composition having 10% of the density of the base composition. In addition, because the mass of the entrained gas is negligible, the concentration of fluoride remains essentially the same in all cases.

In the case where some or all of the density reduction means comprises a low density filler, such as hollow glass or ceramic spheres, there will not be a 1:1 reduction in density as more low density of filler is added. However, the reduction of density is still substantial, even dramatic, so long as the density of the filler is substantially less than the density of the base composition. However, slight adjustments in the fluoride content may be necessary to maintain the desired fluoride concentration in the final dental compositions.

As discussed above, assuming that a "pea-size" amount is ⅓ the "normal amount", then it would be necessary to include enough density reduction means to reduce the density of the base composition by ⅔ to yield a final composition having only ⅓ the density of the base composition. In this way, one can use three times of the reduced density composition compared to the base composition and still put the same amount of fluoride into his or her mouth. Thus, an amount of reduced density toothpaste sufficient to cover an entire adult toothbrush (as depicted in FIG. 3) will, in reality, be equivalent to using a pea-size amount of the base composition (as depicted in FIG. 2).

However, because a child-sized toothbrush is roughly 50% the size of an adult toothbrush, the final dental composition only needs to have a density reduction of ⅓, or 33%. In other words, because the volume of toothpaste required to totally cover the bristles of a child-sized toothbrush is about 50% of the volume required to cover an adult toothbrush, a "pea-size" amount is roughly ⅔ of the volume needed to cover a child-size toothbrush. Thus, assuming that a child will want to cover most or all of the bristles of a child-size toothbrush with toothpaste, a reduced-density dental composition would only need to have a density reduction of about ⅓ in order for the toothbrush-covering amount to be equivalent to the recommended pea-size amount using the foregoing assumptions.

EXAMPLE 3

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 20% |
| Propylene glycol | 35% |
| Flavor and color | 1.5% |
| Sorbitol | 15% |
| Potassium laurate | 1% |
| Polysorbate 60 | 1% |
| Carbomer 974 NF | 1% |
| Abrasive aluminum oxide | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 4

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 20% |
| Propylene glycol | 20% |
| Polyethylene glycol 300 | 15% |
| Flavor and color | 1.5% |
| Xylitol | 15% |
| Octaoxyethlylene glycol monododecyl ether | 1% |
| Polysorbate 20 | 1% |
| Pemulen TR-1 NF | 2% |
| Abrasive aluminum oxide | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 5

Dental compositions suitable for use in brushing or cleaning teeth are made from a base composition having the following components, exclusive of density reduction means, expressed as a percentage by weight of the base composition exclusive of the density reduction means:

| | |
|---|---|
| Glycerin | 31% |
| Polyethylene glycol 300 | 35% |
| Flavor and color | 1.5% |
| Sodium saccharin | 1% |
| Potassium laurate | 1% |
| Polyalkylene oxide modified polydimethyl siloxanes | 1% |
| Sodium oleate | 2% |
| Fumed Silicon dioxide | 2% |
| Abrasive calcium fluorosilicate | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 6

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 63% |
| Flavor and color | 1.5% |
| Phenylalanine | 1% |
| Sodium decane sulfonate | 1% |
| Carbomer 934 | 6% |
| Abrasive aluminum oxide | 27% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 7

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 22% |
| Propylene glycol | 36% |
| Flavor and color | 1.5% |
| Mannose | 15% |
| Tetradecyltrimethyl ammonium bromide | 1% |
| Sodium di-2-ethylhexyl sulfosuccinate | 1% |
| Locust bean gum | 1% |
| Abrasive titanium dioxide | 22% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 8

Dental compositions suitable for use in brushing or cleaning teeth are made from a base composition having the following components, exclusive of density reduction means, expressed as a percentage by weight of the base composition exclusive of the density reduction means:

| | |
|---|---|
| Propylene glycol | 57% |
| Flavor and color | 1.5% |
| Fructose | 15% |
| Carbomer 910 | 4% |
| Abrasive mica | 22% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 9

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 20% |
| Polyethylene glycol | 35% |
| Flavor and color | 1.5% |
| Sorbitol | 15% |
| Abrasive silicon dioxide | 20% |
| Mica | 8% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 10

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 20% |
| Glycerin | 50% |
| Flavor and color | 1.5% |
| Sucralose | 1% |
| Sodium deoxycholate | 2% |
| Abrasive aluminum oxide | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 11

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 23% |
| Polyethylene glycol | 38% |
| Flavor and color | 1.5% |
| Sorbitol | 15% |
| Abrasive silicon dioxide | 22% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 20–90% in 5% increments. The density reduction means may comprise both gases and low density solids as discussed herein. The remaining discussion of Example 2 is incorporated herein by reference.

EXAMPLE 12

The density of any conventional toothpaste is reduced by adding one or more low density, lightweight fillers having a density less than 0.5 g/cc (preferably less than 0.3 g/cc, most preferably less than 0.1 g/cc) in order to reduce the density of the original toothpaste by 20–90% in increments of 5% selected from the following: hollow glass spheres (e.g., made from silica, soda-lime-borosilicate, aluminum oxide, silica-alumina ceramic, or alkali-alumino-silicate ceramic), hollow ceramic spheres, expanded perlite (treated with a sealer), expanded vermiculite (water resistant), aerogels (treated to be water resistant), expanded silica gels, cork, polystyrene foam particles, polyethylene particles. polypropylene particles, and hollow plastic spheres.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental composition for delivering a reduced quantity of fluoride ions into a person's mouth comprising:

a base composition including a fluoride ion source that provides from about 10 ppm to about 3500 ppm of fluoride ions, an abrasive solid, and a carrier selected from the group consisting of liquids, gels, pastes, and mixtures thereof, the base composition having a density; and a density reducing component dispersed throughout the base composition and included in an amount so as to yield a final dental composition having a density that is at least about 30% less than the density of the base composition in order to thereby reduce the quantity of fluoride ions delivered per unit volume of the dental composition by at least about 30% relative to the base composition, wherein at least a portion of the density reducing component comprises a lower density solid filler, wherein the dental composition has a rheology such that it can be expressed onto a toothbrush as a coherent mass and a sufficiently low level of abrasiveness such that it is suitable for use in daily tooth brushing.

2. A dental composition as defined in claim 1, wherein the density reducing component reduces is included in an amount so as to yield a final dental composition having a density that is at least about 50% less than the density of the base composition in order to thereby reduce the quantity of fluoride ions delivered per unit volume of the dental composition by at least about 50% relative to the base composition.

3. A dental composition as defined in claim 1, wherein the density reducing component reduces is included in an amount so as to yield a final dental composition having a density that is at least about 75% less than the density of the base composition in order to thereby reduce the quantity of fluoride ions delivered per unit volume of the dental composition by at least about 75% relative to the base composition.

4. A dental composition as defined in claim 1, wherein a portion of the density reducing component further comprises a gas that is dispersed throughout the base composition during mixing such that the dental composition is pre-foamed.

5. A dental composition as defined in claim 4, wherein the base composition further includes a foaming agent that stabilizes the pre-foamed dental composition such that the dental composition is capable of being stored for a desired period of time within a storage container without significant collapse of the foam.

6. A dental composition as defined in claim 1, wherein the density reducing component consists exclusively of the lower density solid filler.

7. A dental composition as defined in claim 1, wherein the lower density solid filler has a density less than about 0.5 g/cm$^3$.

8. A dental composition as defined in claim 1, wherein the lower density solid filler has a density less than about 0.3 g/cm$^3$.

9. A dental composition as defined in claim 1, wherein the lower density solid filler has a density less than about 0.1 g/cm$^3$.

10. A dental composition as defined in claim 1, wherein the lower density solid filler imparts abrasive activity to the dental composition in addition to the abrasive solid within the base composition.

11. A dental composition as defined in claim 1, wherein the density reducing component comprises a mixture of a gas and the lower density solid filler.

12. A dental composition as defined in claim 1, wherein a portion of the density reducing component comprises initially compressed gas that causes the base composition to foam and expand to form the dental composition upon dispensing the base composition and compressed gas from a storage container onto a toothbrush.

13. A dental composition as defined in claim 12, wherein the compressed gas is premixed with the base composition and wherein the compressed gas and the base composition are initially stored together within a pressurized storage container.

14. A dental composition as defined in claim 12, wherein the compressed gas is stored in a compartment separate from, but in communication with, a storage container, containing the base composition such that the compressed gas is able to mix with the base composition and causes the base composition to foam and expand upon dispensing a mixture of the base composition and compressed gas.

15. A dental composition as defined in claim 1, wherein the fluoride ion source is included in an amount such that the dental composition provides fluoride ions in a concentration in a range from about 850 ppm to about 1150 ppm.

16. A dental composition as defined in claim 1 wherein the dental composition has a volume greater than about 133% relative to the volume of the base composition exclusive of the density reducing component.

17. A dental composition as defined in claim 1, wherein the dental composition has a volume greater than about 150% relative to the volume of the base composition exclusive of the density reducing component.

18. A dental composition as defined in claim 1, wherein the dental composition has a volume greater than about 300% relative to the volume of the base composition exclusive of the density reducing component.

19. A dental composition as defined in claim 1, wherein the dental composition has a rheology so that it may be expressed from a tube.

20. A reduced density dental composition comprising:
   a base composition including a fluoride ion source that provides from about 10 ppm to about 3500 ppm of fluoride ions, all abrasive solid, and a carrier selected from the group consisting of liquids, gels, pastes, and mixtures thereof, the base composition having an density; and
   a lower density solid filler, separate from the abrasive solid, having a density less than about 0.5 g/cm$^3$ and being dispersed throughout the base composition in an amount so as to yield a final reduced density dental composition having a density that is at least about 30% less than the density of the base composition in order to thereby reduce the quantity of fluoride ions delivered per unit volume of the dental composition by at least about 30% relative to the base composition,
   wherein the dental composition has a rheology such that it can be expressed onto a toothbrush as a coherent mass and a sufficiently low level of abrasiveness such that it is suitable for use in daily tooth brushing.

21. A reduced density dental composition as defined in claim 20, wherein the lower density solid filler is included in an amount so as to yield a final reduced density dental composition having a density that is at least about 50% less than the density of the base composition in order to thereby reduce the quantity of fluoride ions delivered per unit volume of the dental composition by at least about 50% relative to the base composition.

22. A reduced density dental composition as defined in claim 20, wherein the lower density solid filler is included in an amount so as to yield a final reduced density dental composition having a density that is at least about 75% less than the density of the base composition in order to thereby reduce the quantity of fluoride ions delivered per unit volume of the dental composition by at least about 75% relative to the base composition.

23. A reduced density dental composition as defined in claim 20, wherein the lower density solid filler has a density less than about 0.3 g/cm$^3$.

24. A reduced density dental composition as defined in claim 20, wherein the lower density solid filler has a density less than about 0.1 g/cm$^3$.

25. A reduced density dental composition as defined in claim 20, wherein the lower density solid filler imparts abrasive activity to the dental composition in addition to the abrasive solid within the base composition.

26. A reduced density dental composition as defined in claim 20, wherein the lower density solid filler comprises an inorganic filler material.

27. A reduced density dental composition as defined in claim 20, wherein the lower density solid filler comprises hollow glass spheres.

28. A reduced density dental composition as defined in claim 20, wherein the lightweight filler material comprises an organic filler material.

29. A reduced density dental composition as defined in claim 20, further including entrained gas.

30. A reduced density dental composition as defined in claim 20, wherein the fluoride ion source is included in an amount such that the dental composition provides fluoride ions in a concentration in a range from about 850 ppm to about 1150 ppm.

31. A reduced density dental composition comprising:
  a base composition including a fluoride ion source that provides from about 10 ppm to about 3500 ppm of fluoride ions, an abrasive solid, and a carrier selected from the group consisting of liquids, gels, pastes, and mixtures thereof, the base composition having a density; and
  at least one of hollow aluminum oxide, ceramic, or glass bubbles separate from the abrasive solid and being dispersed throughout the base composition in an amount so as to yield a final reduced density dental composition having a density that is at least about 30% less than the density of the base composition in order to thereby reduce the quantity of fluoride ions delivered per unit volume of the dental composition by at least about 30% relative to the base composition,
  wherein the dental composition has a rheology such that it can be expressed onto a toothbrush as a coherent mass and a sufficiently low level of abrasiveness such that it is suitable for use in daily tooth brushing.

32. A foamed dental composition for delivering a reduced quantity of flouride ions into a person's mouth comprising:
  a base composition including a fluoride ion source that provides front about 10 ppm to about 3500 ppm of fluoride ions, an abrasive solid, and a carrier selected from the group consisting of liquids, gels, pastes, and mixtures thereof, the base composition having a density, and
  a mixture of a gas and a lower density solid dispersed throughout the base composition, wherein the mixture of the gas and lower density solid is included in an amount so as to yield a final foamed dental composition having a density that is at least about 30% less than the density of the base composition in order to thereby reduce the quantity of fluoride ions delivered per unit volume of the dental composition by at least about 30% relative to the base composition,
  wherein the dental composition has a rheology such that it can be expressed onto a toothbrush as a coherent mass and a sufficiently low level of abrasiveness such that it is suitable for use in daily tooth brushing.

33. A foamed dental composition as defined in claim 32, wherein the mixture of the gas and lower density solid is included in an amount so as to yield a final foamed dental composition having a density that is at least about 50% less than the density of the base composition in order to thereby reduce the quantity of fluoride ions delivered per unit volume of the dental composition by at least about 50% relative to the base composition.

34. A method for delivering a reduced quantity of fluoride ions into a person's mouth, comprising:
  (a) expressing a quantity of a reduced density dental composition as a coherent mass onto a tooth brush suitable for daily brushing, wherein the dental composition has a sufficiently low level of abrasiveness such that it is suitable for use in daily tooth brushing and includes:
    (i) a base composition including a fluoride ion source that provides form about 10 ppm to about 3500 ppm of fluoride ions, an abrasive solid, and a carrier selected from the group consisting of liquids, gels, pastes, and mixtures thereof, the base composition having a density; and
    (ii) a density reducing component dispersed throughout the base composition and included in an amount so as to yield a final dental composition having a density that is at least about 30 less than the density of the base composition in order to thereby reduce the quantity of fluoride ions delivered per unit volume of the dental composition by at least about 30% relative to the base composition, wherein at least a portion of the density reducing component comprises a lower density solid filler; and
  (b) brushing the person's teeth using the tooth brush and the dental composition.

35. A method as defined in claim 34, wherein the density reducing component further includes a gas.

36. A method as defined in claim 34, wherein the density reducing component consists exclusively of the low density solid filler.

* * * * *

UNITED STATES PATENT AND TRADEMARK OFFICE
CERTIFICATE OF CORRECTION

PATENT NO. : 6,139,820
DATED : October 31, 2000
INVENTOR(S) : Dan E. Fischer; Steven D. Jensen It is certified that error appears in the above-identified patent and that said Letters Patent is hereby corrected as shown below:

Column 5,
Line 27, after "0.3" change "g/m$^3$" to -- g/cm$^3$ --

Column 8,
Line 65, after "FIG.1" change "weights" to -- weighs --

Column 11,
Line 62, after "have a" change "ph" to -- pH --

Column 12,
Lines 11-12, after "inorganic" and before "organic" insert -- or --

Column 13,
Line 56, after "palmitoyl" change "taurides" to -- laurides --

Column 14,
Line 9, after "invention" and before "at a" delete [is]

Column 16,
Line 13, change "acrogels" to -- aerogels --

Column 19,
Line 50, after "roughly" change "increase" to -- increases --

Column 27,
Line 14, after "component" delete [further]

Column 28,
Line 17, after "having" change "an" to -- a --

Column 29,
Line 29, after "provides" change "front" to -- from --

UNITED STATES PATENT AND TRADEMARK OFFICE
CERTIFICATE OF CORRECTION

PATENT NO. : 6,139,820
DATED : October 31, 2000
INVENTOR(S) : Dan E. Fischer; Steven D. Jensen It is certified that error appears in the above-identified patent and that said Letters Patent is hereby corrected as shown below:

<u>Column 30,</u>
Line 20, after "provides" change "form" to -- from --
Line 28, after "about" change "30" to -- 30% --
Line 37, after "wherein" insert -- a portion of --

Signed and Sealed this

Thirteenth Day of November, 2001

Attest:

*Nicholas P. Godici*

NICHOLAS P. GODICI
*Attesting Officer*  *Acting Director of the United States Patent and Trademark Office*